United States Patent [19]

Sun

[11] Patent Number: 5,263,376
[45] Date of Patent: Nov. 23, 1993

[54] SAMPLE-TAKING DEVICE FOR A STORAGE TANK

[76] Inventor: Justin Sun, No. 15-1, Lane 300, Kai Feng Rd., Hsin Hsing Dist., Kaohsiung, Taiwan

[21] Appl. No.: 780,207

[22] Filed: Oct. 22, 1991

[51] Int. Cl.⁵ .................. G01N 1/12; G01N 1/16
[52] U.S. Cl. ................... 73/864.31; 73/863.82; 73/863.86; 33/717
[58] Field of Search .......... 73/864.31, 863.82, 863.86, 73/854.63, 864.66, 64.56; 33/717, 718

[56] References Cited

U.S. PATENT DOCUMENTS

| | | | |
|---|---|---|---|
| 1,818,753 | 10/1931 | Spikes | 73/864.31 X |
| 1,870,436 | 8/1932 | Ball et al. | 33/717 X |
| 1,974,236 | 9/1934 | Contacuzene | 73/864.31 X |
| 2,006,301 | 6/1935 | Meyer | 73/864.31 X |
| 2,255,369 | 9/1941 | Spaeth | 73/864.31 X |
| 2,261,457 | 11/1941 | Wiggins | 73/864.31 X |
| 2,411,157 | 11/1946 | Fene et al. | 73/864.31 |
| 2,934,959 | 5/1960 | Johnson | 73/863.82 |
| 3,121,334 | 2/1964 | Bott | 73/863.82 |
| 3,129,513 | 4/1964 | Porter | 73/864.65 X |
| 4,196,627 | 4/1980 | Locker | 73/864.31 |
| 4,947,592 | 2/1984 | Haller | 33/717 X |

Primary Examiner—Tom Noland
Attorney, Agent, or Firm—Jacobson, Price, Holman & Stern

[57] ABSTRACT

A sample-taking device for a storage tank able to take samples from the stored liquid at any depth out of the tank through a sample inlet sustained on a float holder able to be moved up and down in the stored liquid by means of a holder moving device operated by a windable handle rotating a gear unit for pulling a rope in the holder moving device.

4 Claims, 4 Drawing Sheets

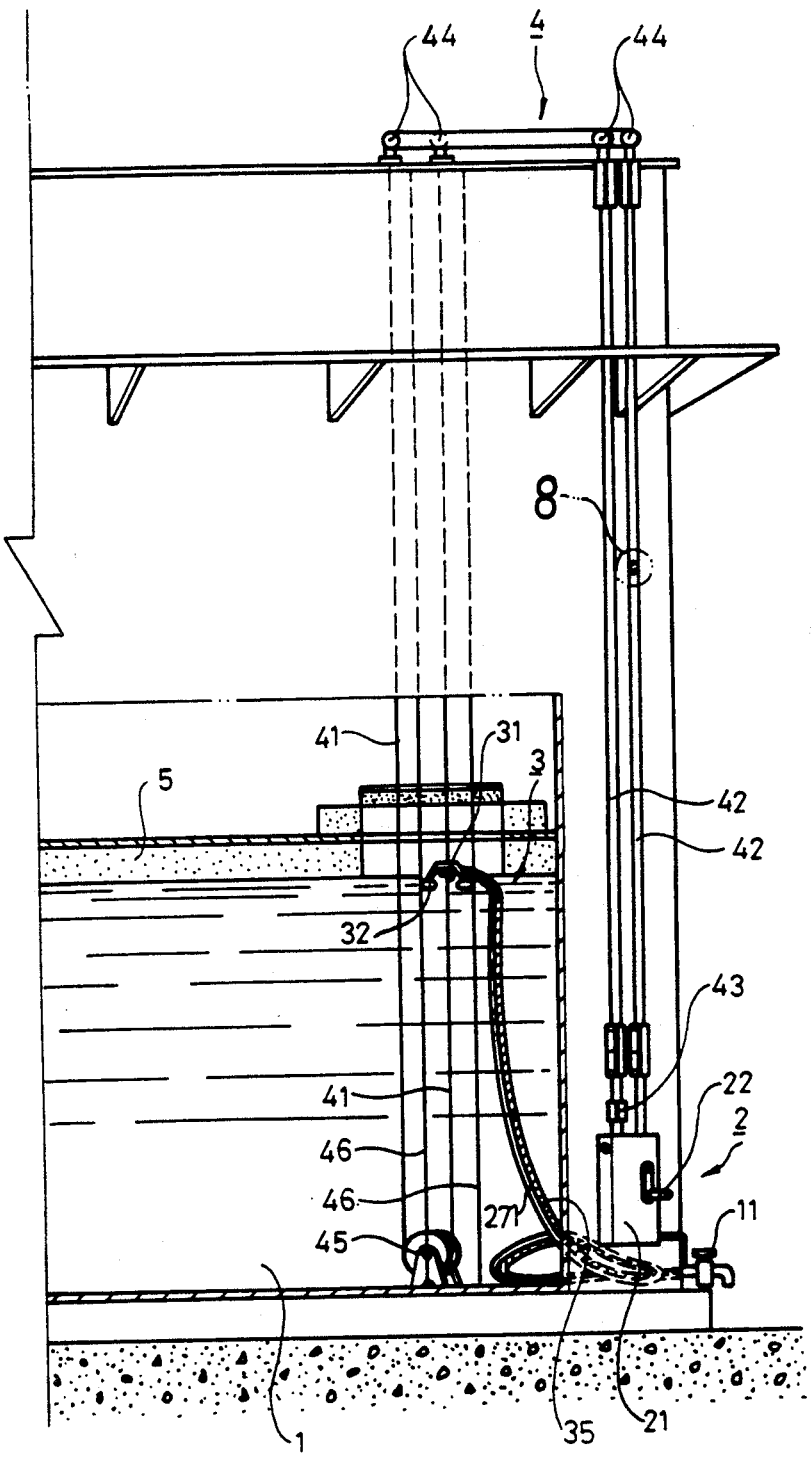
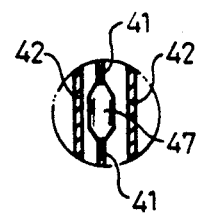
FIG.8
FIG.7

SAMPLE-TAKING DEVICE FOR A STORAGE TANK

BACKGROUND OF THE INVENTION

A conventional method of taking a sample from a storage tank as performed by a worker who climbs up to the top of the tank and lowers down a bottle or container in the tank for taking a sample. But a precise sample may be hard to get with such a method, and in addition, climbing up a tank high as 20, 30, or 40 meters involves risk, especially if the tank stores oil or chemicals having high temperature or toxicity.

SUMMARY OF THE INVENTION

This invention has been devised to supply a sample-taking device to be provided partly inside and partly outside a storage tank, able to take samples of stored liquid from any depth in the tank. The process is simple and safe.

The sample-taking device of the present invention comprises a sample inlet sustained by a float inlet holder able to be moved up and down in stored liquid by means of a rope to be moved up and down by a gear unit to be rotated by a winding handle and a chain wheel combined with the gear unit for pulling a chain. The ample inlet is connected with a tube leading to a valve fixed outside the tank through which the sample following in the inlet through the tube can go out or be stopped, with the aid of a sensor to send a sensed signal to gauges through a signal cord so that a sample can be taken from any depth in the stored liquid in the tank.

BRIEF DESCRIPTION OF THE DRAWINGS

FIG. 7 is a view similar to FIG. 1 of a second embodiment of the sample-taking device of the present invention.

FIG. 8 is a magnified view of part 8 in FIG. 7.

DETAILED DESCRIPTION OF THE INVENTION

Figure 1:
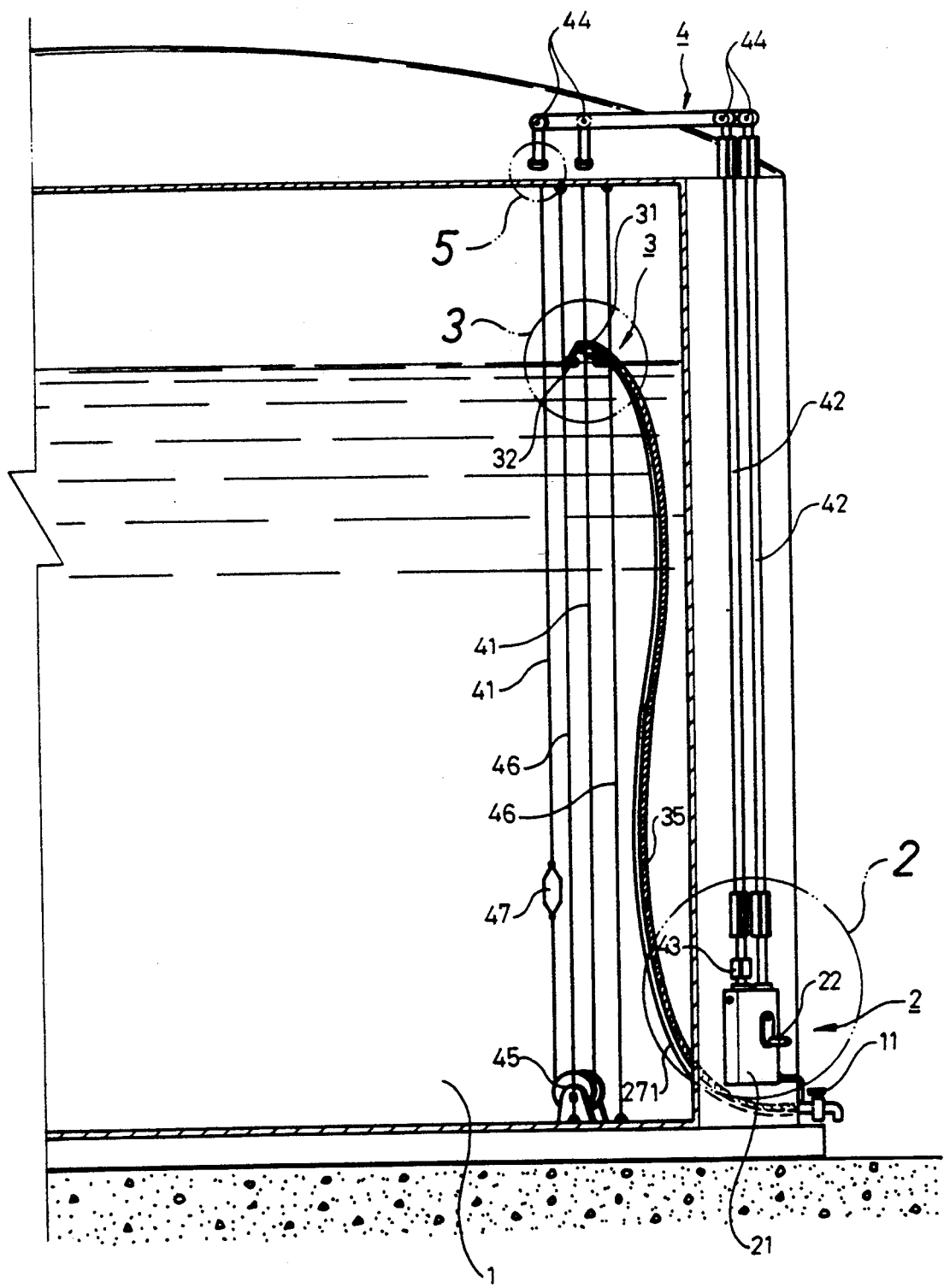
FIG. 1 is a schematic view of a first embodiment of a sample-taking device of the present invention.

The first embodiment of the sample-taking device for a storage tank, as shown in FIG. 1, comprises a control case 2, a sample-taking apparatus or holder 3, a holder moving means 4 as its main components provided partly inside and partly outside a store tank.

Figure 2:
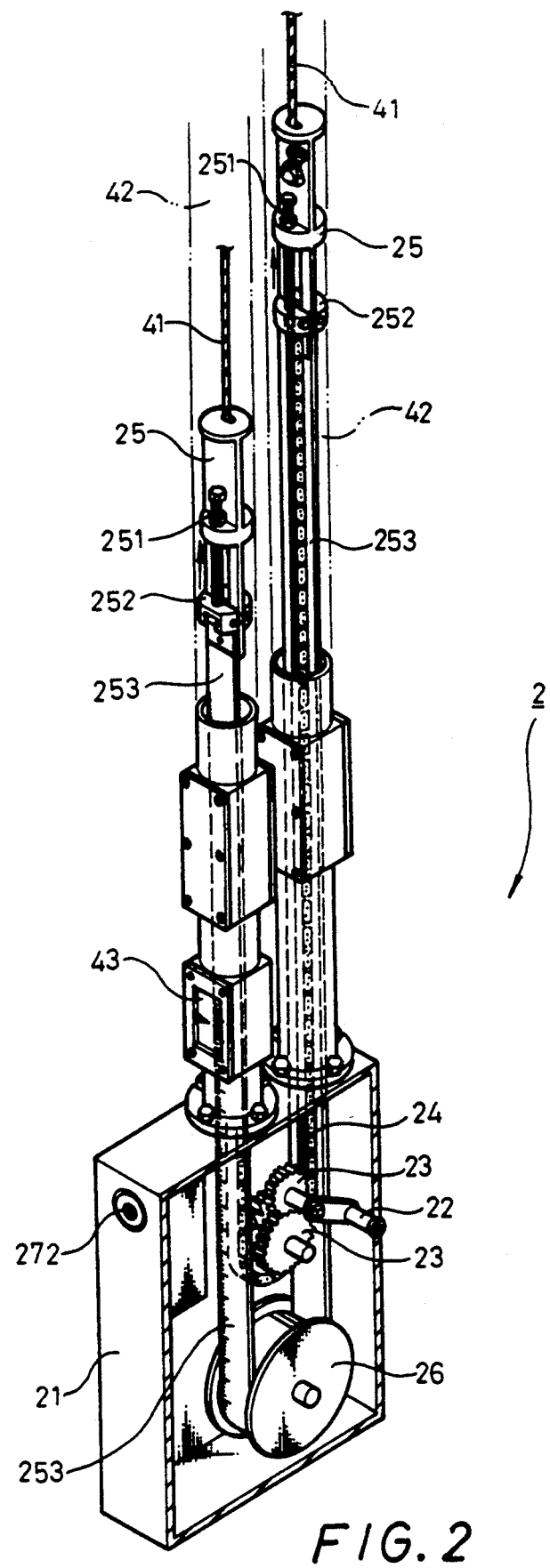
FIG. 2 is a magnified perspective view of part 2 in FIG. 1.
Figure 3:
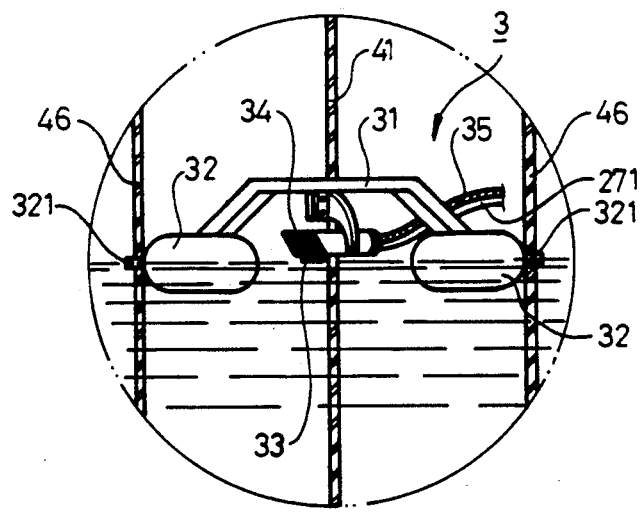
FIG. 3 is a magnified view of part 3 in FIG. 1.
Figure 4:
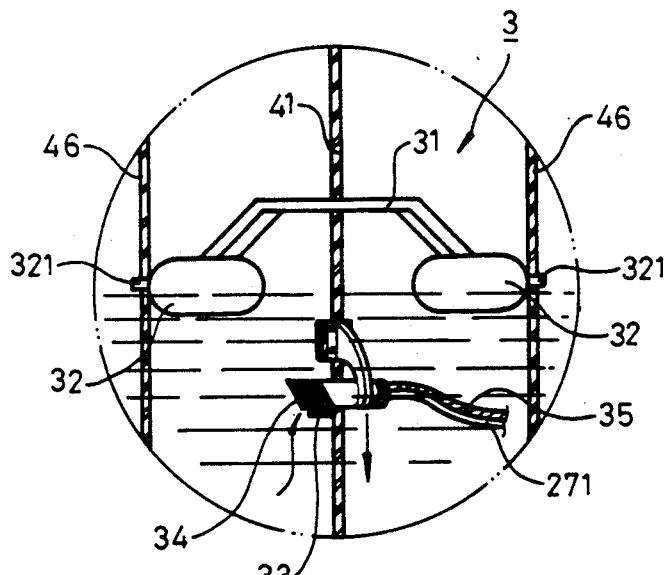
FIG. 4 is an operational view of part 5 in FIG. 3.

The control case 2 shown in FIGS. 1, 2 has a stationary case body 21 mounted on the floor outside a store tank 1, a windable handle 22 extending from inside the case body 21, a gear unit 23 also therein for being rotated by the handle 22, the last gear in the gear unit 23 combined with a chain gear to move a chain 24 engaging the chain gear and two connecting bases 25 above and outside the case body 21 for two ends of the chain 24 respectively to be connected with. The connecting bases 25 each have an upper end for two ropes 42 of the holder moving means 4 to be bound firmly with, and a threaded hole for an adjusting bolt 251 to screw with. The adjusting bolts 251 have the ends able to pull and move two movable bases 252 which respectively connect firmly with two ends of a band scale 253 having measuring marks and extending around a turning wheel 26 fixed in the case body 21. In order to prevent the chain 24 and the band scale 253 from being contaminated, they are surrounded by two tubes 42 of the holder moving means 4, to move therein. One of the tubes 42 has a check window 43, through which the measuring marks on the band scale 253 can be read. The case body 21 also has a socket 272 to receive a signal cord 271 connected with a sensor 33 provided at a sample inlet 34 so that the sensor 33 can send signals for the height and the temperature of the liquid stored in the tank to the socket 272 and then to gauges (not indicated in the drawings).

The sample-taking apparatus 3 includes a sample taking device or inlet 34 fixed firmly on a rope 41, which can be pulled to move up and down so as to move the sample inlet 34 together in the same way to float on the surface of the liquid or to immerse therein. A float holder 31 is provided above the inlet 34, connected with two floats 32 at both ends. Each float 32 has a sidewise foot 321 for a guide rope 46 to pass through so that the float holder 31 can move up and down freely guided by the two guide ropes 46, but generally floats on the surface of the stored liquid by means of buoyancy of the floats 32. The rope 41 has a weight 47 at a proper place to keep the inlet 34 raised but restricted by the float holder 31 to be located to float a little higher than the surface of the stored liquid. In taking a sample, the liquid can enter the inlet 34 to flow down through a soft tube 35 extending out of the tank 1, going out of the valve 11 connected with the end of the tube 35. A sensor 33 is provided under the inlet 34, sending a sensed-out signal to the socket 272 through the cord 271.

Figure 5:
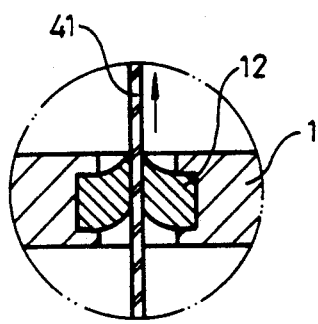
FIG. 5 is a magnified view of part 5 in FIG. 1.
Figure 6:
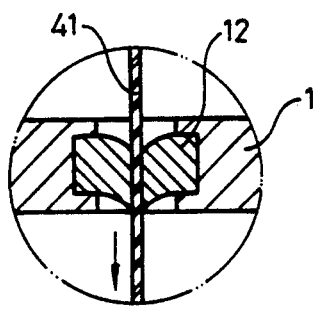
FIG. 6 is an operational view of FIG. 5.

The holder moving means 4 includes a rope 41 having its two ends separately connected firmly with two connecting bases 25. The rope 41 extends to pass around two guide wheels 44 on the top surface of the store tank 1 and extends down to pass around a return wheel 45 fixed on the bottom of the tank 1. The rope 41 is also connected with the float holder 31, keeping the holder 31 in stable condition to float up and down with the surface of the stored liquid with the aid of two guide ropes 46 at both sides of the rope 41, and the guide ropes 46 pass through the two feet 321 of the floats 32, helping the holder 31 to move up and down stably and steadily. The hole in the wall of the tank 1 through where the rope 41 passes is provided with a rubber gasket 12, as shown in FIGS. 5, 6, to prevent friction between the rope 41 and the tank 1, and leakage of the stored liquid out of the tank as well Next, operation of the device is to be described. Winding around the windable handle 22 causes the chain 24 to move up and down, which then pulls up and down the rope 41. Thus the sample inlet 34 is moved to go up and down, and its moving distance can be read from the band scale 253, which can be adjusted correctly by rotating the adjusting bolts 251—one being slackened and the other tightened—on the bases 25, if the band scale 253 is biased. The location of the inlet 34 can be changed by winding the windable handle 22 and the depth of the inlet 34 in the stored liquid can be checked by looking through the check window 43 so that the quality of the stored liquid at any depth can be checked by taking samples from the liquid at any depth through the valve 11.

The second embodiment of this invention, as shown in FIGS. 7, 8 is to be utilized for a storage tank 1 having a floating cover 5 to float directly on the surface of a stored liquid, having the same components as the first embodiment provided in the same manner, except that the rope 41 and the guide ropes 46 pass through the cover 5 and the weight 47 connected with the rope 41 for always pulling up the inlet 34 is contained in a protective tube 42 fixed outside of the tank 1, to avoid blocking rising movement of the cover 5.

What is claimed is:

1. A sample-taking device for a liquid storage tank comprising;

a control case fixed stationary on the outside of a storage tank, the control case having a windable handle, a gear unit connected to the handle to rotate a chain wheel, a chain wheel and a chain engaging the chain wheel, two connecting bases respectively connected with opposite ends of the chain and each connecting base being connected with one end of a transmission rope, said rope extending up the outside of tank to pass around two guide wheels on top of the tank and down the inside of the tank to pass around a return wheel, said bases being respectively connected with opposite ends of a band scale extending to pass around a turning wheel in the control case;

a sample-taking apparatus in the tank including a sample-taking inlet and a sensor mounted on the transmission rope for up and down movement in liquid in the tank when the rope is moved by operation of said handle, and a float holder combined with two guide ropes in the tank, the sensor and the sample-taking inlet located under the float holder, said sensor being connected with a signal cord leading to a socket fixed on the control case, and said inlet being connected with a tube extending to and connected with a control valve extending out from a wall of the tank.

2. The sample-taking device as claimed in claim 1, wherein the two connecting bases pull the transmission rope when the windable handle is wound, and therefore, the sample inlet mounted on the rope is moved up and down, and the band scale is at the same time moved up and down by the turning wheel, showing the height of the sample inlet, being read through a check window.

3. The sample-taking device as claimed in claim 1, wherein the band scale has two ends connected separately with two movable bases, which are connected with the two connecting bases by means of two bolts, and the bolts are adjustably screwed to pull two movable bases nearer to the two connecting bases so as to adjust the band scale.

4. The sample-taking device as claimed in claim 1, wherein the float holder includes two floats each having a sidewise foot for one guide rope to pass through, sand said guide ropes are located at opposite sides of the transmission rope, each guide rope having one end thereof fixed stationary at the top of the tank and an opposing end thereof fixed stationary at a bottom of the tank.

* * * * *